United States Patent
Thomas et al.

[19]

[11] Patent Number: 6,061,125
[45] Date of Patent: May 9, 2000

[54] DUAL ILLUMINATION APPARATUS FOR CONTAINER INSPECTION

[75] Inventors: Alan E. Thomas; Michael C. Bagley, both of Clearwater, Fla.

[73] Assignee: Insight Control Systems International, Safety Harbor, Fla.

[21] Appl. No.: 09/014,052

[22] Filed: Jan. 27, 1998

[51] Int. Cl.[7] .................................................... G01N 21/00
[52] U.S. Cl. ..................... 356/237; 356/239; 356/240; 356/428
[58] Field of Search .................... 356/237, 239, 356/240, 428

[56] References Cited

U.S. PATENT DOCUMENTS

| | | | |
|---|---|---|---|
| 4,606,635 | 8/1986 | Miyazawa et al. | 356/240 |
| 4,733,973 | 3/1988 | Machak et al. . | |
| 4,758,084 | 7/1988 | Tokumi et al. . | |
| 4,778,999 | 10/1988 | Fisher . | |
| 4,791,287 | 12/1988 | Fisher . | |
| 4,899,573 | 2/1990 | Dimmick et al. . | |
| 5,030,823 | 7/1991 | Obdeijn | 356/240.1 |
| 5,220,400 | 6/1993 | Anderson et al. | 356/240.1 |
| 5,365,084 | 11/1994 | Cochran et al. . | |
| 5,388,707 | 2/1995 | Stivison et al. . | |
| 5,451,773 | 9/1995 | Triner et al. . | |
| 5,532,605 | 7/1996 | Dimmick et al. . | |
| 5,558,233 | 9/1996 | Dimmick et al. . | |
| 5,592,286 | 1/1997 | Fedor | 356/240.1 |
| 5,604,442 | 2/1997 | Dimmick et al. . | |

*Primary Examiner*—Frank G. Font
*Assistant Examiner*—Reginald Ratliff
*Attorney, Agent, or Firm*—Frederick L. Tolhurst

[57] ABSTRACT

A container inspection system wherein diffused light and collimated light provide backlighting to image a container (10) by a color camera (18). Light strobed through a ring light (36) and parabolic reflector (39) is diffused at a diffusion laminate (46). Light strobed through a ring light (60) and parabolic reflector (64) is collimated at lens (68) and aligned with the diffused light by reflector laminate (48). Diffused light is filtered by a blue band-pass filter (42) and collimated light is filtered by a red band-pass filter (66) and camera (18) segregates the container image according to blue and red color planes.

12 Claims, 3 Drawing Sheets

DUAL ILLUMINATION APPARATUS FOR CONTAINER INSPECTION

BACKGROUND OF THE INVENTION

1. Field of the Invention

The subject invention is directed to automated systems for container inspection and, more particularly, automated systems for optically inspecting transparent and translucent containers for composition defects.

2. Description of the Prior Art

Various systems for inspecting containers are known in the prior art. Those systems were often used to inspect refillable transparent or translucent containers for foreign materials after the containers were washed, but before they were refilled. However, it was also found that such systems were useful in identifying certain material defects in the containers. Defects such as "stones" (refractory particles) and "seeds" (air bubbles) represented potential failure points and those inspection systems also came to be used by container manufacturers as well as fillers to inspect containers at the time of manufacture.

Generally, in these prior systems a rotating prism projects an image of the bottom of the container through a lens and onto an array of photosensors that are arranged in a fixed circle. Each photosensor is responsive to an area of the container bottom that defines a circular band within the container image. In combination, the circular bands cover the entire area of the container bottom.

One disadvantage of these systems has been that they require precise placement of the container with respect to the rotating prism. Often this positioning is accomplished by a star-wheel mechanism that required costly changeover parts to accommodate containers of different sizes and shapes.

In recent years, improvements in solid-state cameras have led to higher image resolution capability and lower overall cost for inspection systems. Improvements in commercially available vision engines have also allowed more accurate interpretation of such higher-resolution images. In some applications, those improvements have allowed cameras to replace the combination of the spinning prism and photosensor array that was used in prior art inspection systems. Thus, the improved camera technology avoided the requirement for precise positioning of the containers and allowed side-transfer belts to be used to convey the containers over an inspection location. Side-belt conveyors were used because they allowed the container to be viewed through the bottom. The side-belt conveyors were also preferable for the reason that they were mechanically simpler than the star-wheels and did not require parts changes to accommodate different container sizes and shapes.

In detecting defects in the containers, in some applications it was found that the improved sensitivity of the camera inspection system had to be compromised to avoid false positive responses to stippling, identification or decoration that was embossed into the bottom of the container or to avoid confusion with baffle marks, cut off scars or other non-stress related defects. To avoid this problem, a diffused light source sometimes has been used to illuminate the bottom of the container. The diffused light source masks the embossing and glass molding marks found on some containers and makes opaque, stress-related defects easily distinguishable. However, this technique also masks some non-opaque defects that represent potential failure points or that are otherwise objectionable.

In the prior art, inspection systems have attempted to compensate for these shortcomings by distancing the diffuse illumination system from the bottom of the container. This practice was found to make non-opaque defects more apparent, but it also increased the rate of false positive indications caused by permissible irregularities or embossed areas in the bottom of the container.

In some instances, container manufacturers have attempted to overcome the difficulties of false positives in bottom inspection systems by eliminating the use of molding marks on the bottom of the containers. However, that also bars the display of helpful information that can be embossed on the container. For example, binary cavity identification techniques are helpful in correlating container defects with particular mold cavities. This information has been used to improve manufacturing efficiency. However, such techniques generally employ the molding of concentric rings, dots or other binary cavity information into the base of the container. Such mold identification techniques conflict with the use of bottom inspection systems.

As a compromise to eliminating the use of any mold cavity identification system, some manufacturers have employed a heel code system wherein the bar code is embossed on the heel of the container instead of on the bottom. This facilitates the use of a bottom inspection system, but has the disadvantage that it requires that the container must be stopped and rotated to read the code. Moreover, when the container is not round so that it can be easily rotated, such heel code systems are not available.

Accordingly, in the prior art there existed a need for a bottom inspection system that could readily discriminate opaque defects as well as other defects, and that was compatible with established methods for providing the container with cavity mold identification and other information or décor embossed thereon.

SUMMARY OF THE INVENTION

In accordance with the subject invention, a first light generator emits light within a first frequency bandwidth and a second light generator emits collimated light within a second frequency bandwidth. A diffuser diffuses light from the first light generator before it illuminates a container. Light from the second light generator also illuminates the container and, together with the diffused light, provides backlighting for a camera. The camera images the container and filters the image to segregate the diffused light image and the collimated light image.

Preferably, the collimated light from the second light generator is reflected to align the pathway of the collimated light to coincide with the pathway of the diffused light.

Also preferably, the bandwidth of the first light generator corresponds to one of the colors blue, red and yellow in the visible light spectrum and the bandwidth of the second light generator corresponds to another of the colors blue, red and yellow in the visible light spectrum.

Most preferably, a laminar element having a diffusion laminate and a reflector laminate diffuses the light from the first light generator and reflects the collimated light from the second light generator so that the pathway of the collimated light coincides with the pathway of the diffused light.

Other objects and advantages of the invention disclosed herein will become apparent to those skilled in the art as a description of a preferred embodiment of the invention proceeds.

BRIEF DESCRIPTION OF THE DRAWINGS

A presently preferred embodiment of the invention disclosed herein is shown and described in connection with the accompanying drawings wherein.

PREFERRED EMBODIMENT OF THE INVENTION

Figure 1:
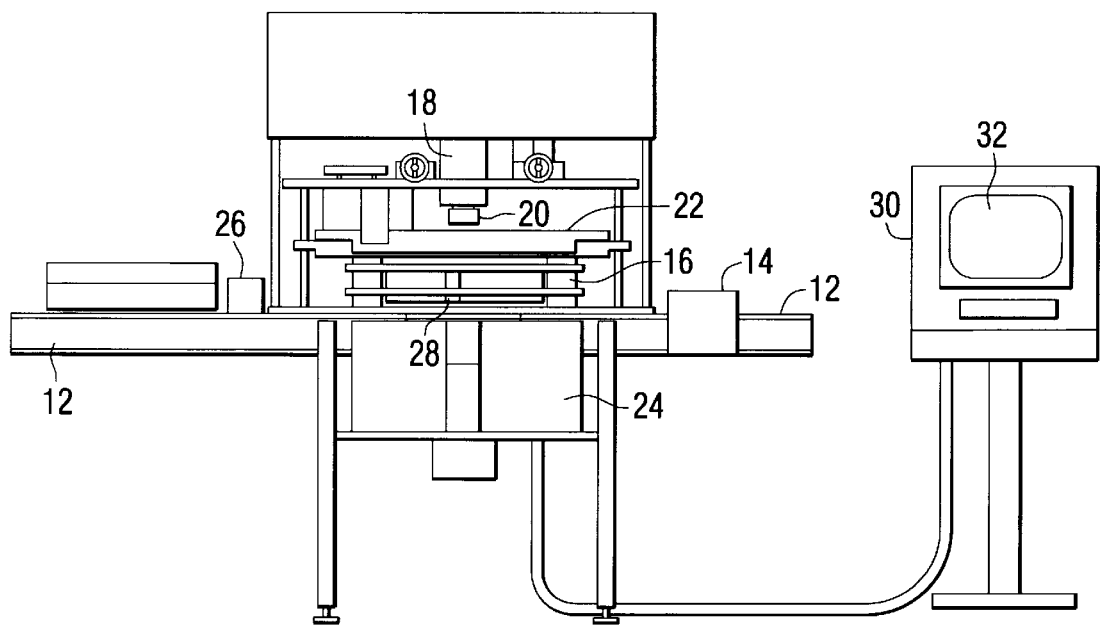
FIG. 1 is a schematic of the system herein disclosed for optically inspecting containers.
Figure 2:
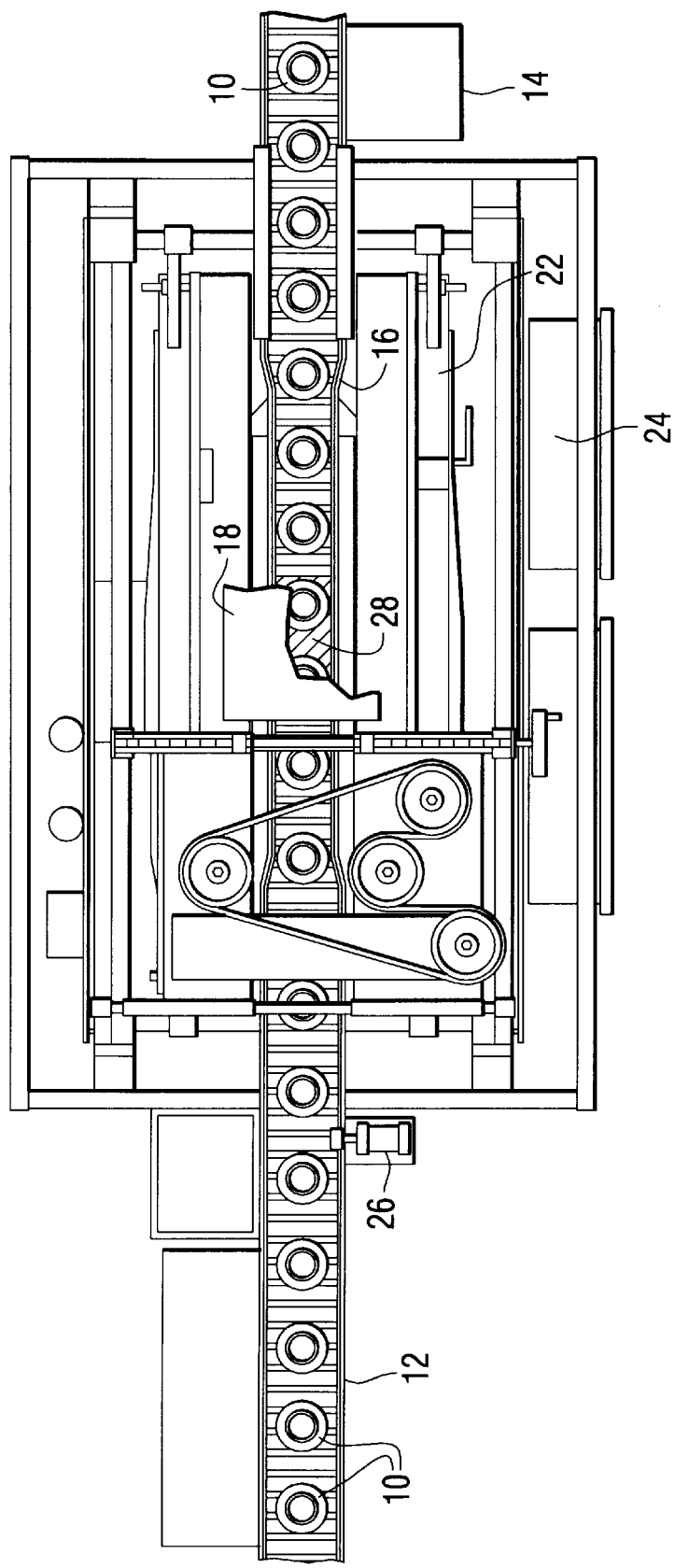
FIG. 2 is a plan view of the schematic shown in FIG. 1.
Figure 3:
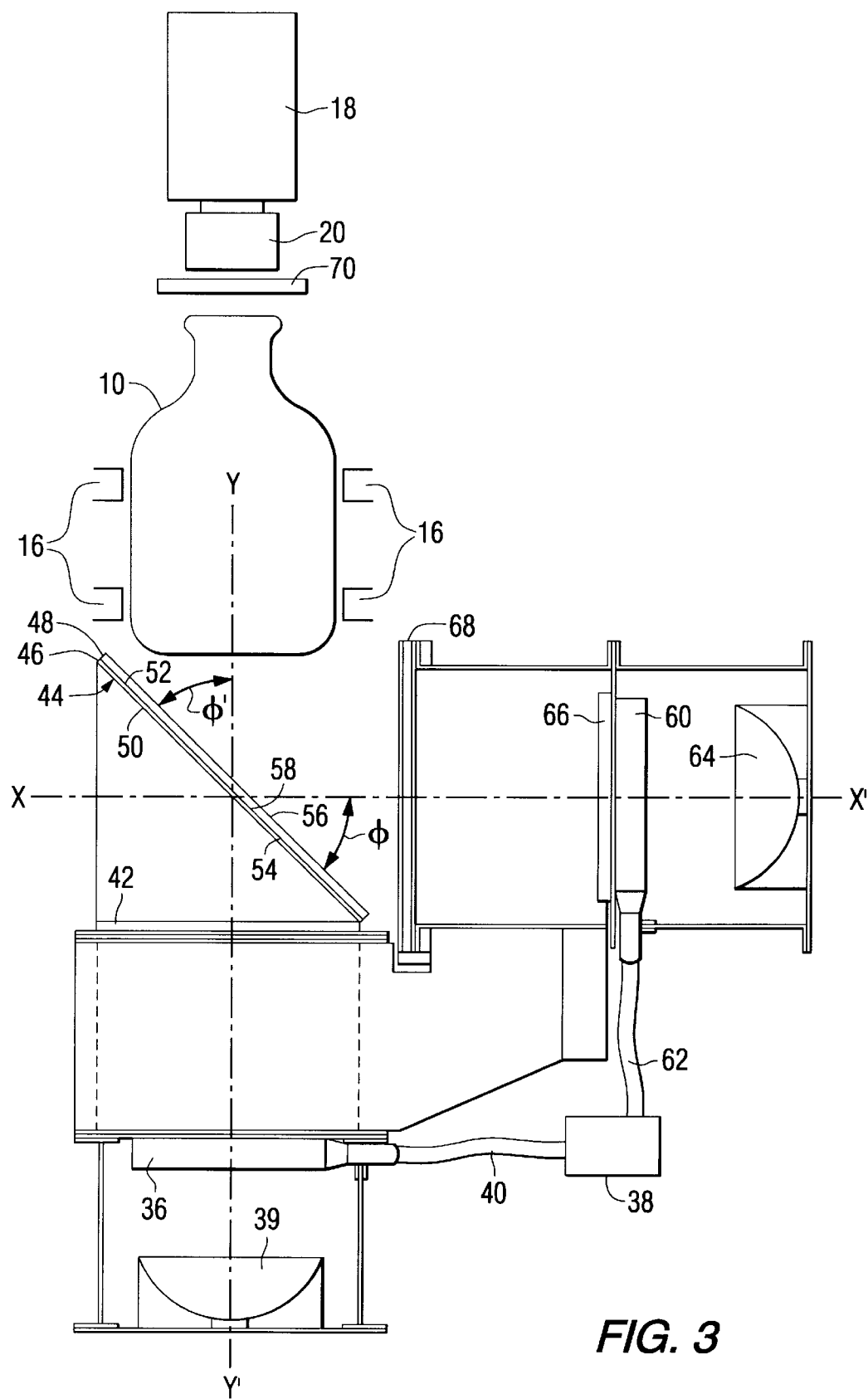
FIG. 3 is an elevation view of a partial section of the apparatus disclosed in FIGS. 1 and 2.

The preferred embodiment of the optical inspection system herein disclosed is illustrated in FIGS. 1–3. As will be understood by those skilled in the art, a workpiece such as container 10 travels on a conveyor line 12 toward the location for inspection. As the containers 10 enter the inspection station, the containers are spaced by an infeed spacing assembly 14 of a type such as is commercially available. The containers are then engaged by a side-belt drive assembly 16. Side-belt drive assembly 16 advances container 10 to an inspection location that is in the field of view of camera 18 having a lens 20. An infeed sensor 22 detects the location of the container and a drive belt encoder is electrically connected to a programmable controller 24. As known to those skilled in the art, programmable controller 24 monitors electrical signals from the encoder to determine the position of the container relative to the inspection location In this way, the inspection system encoder monitors the location of the container as it travels through the side-belt drive assembly 16.

As also understood by those skilled in the art, conveyor 12 transfers container 10 away from side-belt drive assembly 16. A rejector assembly 26 is located adjacent to conveyor 12 and is also electrically connected to controller 24. Rejector assembly 26 is an electro-mechanical device such as a solenoid or equivalent device that produces movement of a mechanical arm in response to electrical control signals from controller 24. Upon receiving a command signal from controller 24, rejector assembly 26 is activated to cause the mechanical arm to intercept the selected container. In this way, command signals from controller 24 cause containers that have been determined to be defective to be separated from containers that have passed acceptance tests as hereafter more fully explained.

As shown in FIGS. 1–3, when container 10 is at the inspection location it is also positioned in the field of view of camera 18. As hereafter more fully described, a controller then causes camera 18 to image container 10 through lens 20. Camera 18 is electrically connected to a camera interface that is located in a console 28. As known to those skilled in the art, the camera interface is electrically connected to a process computer 30 and provides an interface point between the camera and the process computer and also between the illumination system that is hereinafter more fully disclosed and the process computer 30. As is known to those skilled in the art, video signals representing the image of the container are transmitted from camera 18 to the interface which stores the image information. The process computer 30 communicates with the camera interface to compare the container image with predetermined image parameters. The image parameters are determined and selected to identify manufacturing defects such as bubbles and seeds. Based on that comparison, the computer 30 determines whether the predetermined parameters of the stored image are within tolerance limits. If the container image is not within tolerance limits, computer 30 transmits a signal to controller 24 and controller 24 activates rejector assembly 26 to cause the container to be rejected. If the container image is within tolerance limits, the computer transmits no signal and the container is retained.

The predetermined parameters that the computer uses for comparison are subject to modification. To this end, the console further includes a monitor 32 and a keyboard that are electrically connected to the computer 30. Monitor 32 is responsive to electrical output signals from the computer 30 to produce visual images on a monitor screen 32. Also, keystrokes by a human operator to the keyboard are translated to electrical signals and provided as input control signals to the computer. In this way, the operator can affect the operation of the computer such as, for example, by modifying certain parameters and parameter values on which the computer makes an acceptance/rejection comparison.

As more specifically shown and described in connection with FIG. 3 the inspection system herein disclosed incorporates two separate light generators that are pulsed by a strobe assembly to illuminate container 10. The container image resulting from each light source is then separated by frequency to afford enhanced inspection of the container, including analysis for defects.

More specifically, controller 24 is electrically connected to a strobe assembly 38. When controller 24 determines that container 10 is at the inspection location, controller 24 provides electrical input signals to strobe assembly 38 and strobe assembly 38 provides pulses of light.

A first light generator is located in opposing relationship to camera 18 and is oriented to direct light toward lens 20. The first light generator includes an annular light source such as a ring light 36 although other light sources could also be used. Ring light 36 emits diffused light in response to light input signals. Strobe assembly 38 is connected to a ring light 36 by a fiber optic bundle 40 and the light pulses are conducted to ring light 36 through fiber optic bundle 40.

The first light generator further includes a parabolic reflector 39 and a first light filter 42. The output light emitted from ring light 36 is reflected by parabolic reflector 39 and redirected through the center of ring light 36 toward first light filter 42. Light filter 42 passes light within a predetermined frequency bandwidth and rejects light that is outside of said predetermined bandwidth. In the specific example of the preferred embodiment, the predetermined bandwidth is in the visible light spectrum and corresponds to the color blue.

Filtered light from filter 42 illuminates a diffusion element that produces diffused light in response to light from the first light generator. In the example of the preferred embodiment, the diffusion element is included in a laminar element 44 that has a diffusion laminate 46 and a reflector laminate 48. Diffusion laminate 46 has planar surfaces 50 and 52 and reflector laminate 48 has planar surfaces 54 and 56. Planar surface 52 of diffusion laminate contacts planar surface 54 of reflector laminate to form an interface 58.

Diffusion laminate 46 is comprised of a thin, translucent material having a textured surface such as paper. Reflector laminate 48 is preferably comprised of glass or a half-silvered mirror that is partially reflective of light as hereafter more fully explained. Light that passes light filter 42 and illuminates planar surface 50 of diffusion laminate 46 is diffused as it passes through the diffusion laminate toward interface 58. At interface 58 the diffused light passes from planar surface 54 of reflector laminate 48 to planar surface 56. Diffused light from planar surface 56 travels toward container 10 and lens 20 of camera 18 to provide diffused backlighting of container 10 during the imaging process.

In a similar fashion, a second light generator emits collimated light within a predetermined frequency bandwidth in response to a trigger signal. Said second light generator includes a ring light 60 that is connected to strobe assembly 38 through a fiber optic bundle 62. The second light generator also includes a parabolic reflector 64, a second light filter 66, and a collimated lens 68.

In the operation of the second light generator, when controller 24 provides a trigger signal to strobe assembly 38, the strobe assembly transmits an illumination pulse through fiber optic bundle 62 to ring light 60. The output light emitted from ring light 60 is reflected by parabolic reflector 64 and redirected through the center of ring light 60 toward second light filter 66.

Light filter 66 passes light within a predetermined frequency bandwidth and reflects light that it outside of said predetermined bandwidth. In the specific example of the preferred embodiment, the predetermined bandwidth of filter 66 is in the visible light spectrum and corresponds to the bandwidth for the color red.

Filtered light from filter 66 illuminates a collimated lens 68 of a type that is commercially available such as a fernell lens. Collimated lens 68 emits collimated light in response to light from filter 66. The collimated light illuminates reflector laminate 48 of laminar element 44. Some of the collimated light is reflected off surface 56 of reflector laminate 48 and additional collimated light is reflected from surface 54 which, in this preferred embodiment, is half-silvered so as to reflect light. Surface 54 is halfsilvered because diffused light from diffusion laminate must also pass surface 54 to reach container 10 and color camera 18. The direction of the reflected collimated light is determined by the orientation of collimated lens 68 and reflector laminate 48 with the collimated light being reflected from reflector laminate 48 at substantially the converse angle as the angle of incidence of the collimated light from collimated lens 68.

In the preferred embodiment, collimated lens 68 and the second light generator are oriented on a longitudinal axis x–x' that is substantially orthogonal to the longitudinal axis y–y' of the first light generator that illuminates diffusion laminate 46 with diffused light. Also, laminar element 44 is oriented such that interface 58 is in a plane that substantially bisects the included angle between those axes. In this way, the angle of incidence of ø collimated light on reflector laminate 48 is substantially 45° and the angle of reflection ø' is also substantially 45°. This angle of reflection places the collimated light that is reflected from reflector laminate 48 substantially in-line with the diffused light from light filter 42. The combined diffused and collimated light is then directed toward container 10 and the lens 20 of camera 18.

The combined diffused and collimated light illuminates container 10 and provides backlighting for camera 18 to image container 10 through lens 20. As discovered in connection with prior container inspection systems, the diffused light is preferred for identifying opaque defects such as stones (refractory particles, etc.) or seeds (bubbles) and obscuring code indicia that are embossed on the container.

In contrast, the collimated light is preferred for imaging embossed indicia that are used for cavity identification or otherwise, as well as certain clear defects that are indistinguishable in diffused light. The diffuse and collimated light sources illuminate container 10 simultaneously and at the same location.

The combined diffuse and collimated light can be separated at camera 18 due to the difference in frequency of the two illumination sources. The diffuse light is in the band-pass frequency of filter 42 which, in the preferred embodiment, is blue. The collimated light is in the band-pass frequency of filter 66 which, in the preferred embodiment, is red. The combined diffused and collimated light is separated at camera 18 by filtering the combined light with corresponding filters after it has passed the container 10. In this way, information regarding opaque defects is processed from the diffused light and information regarding cavity information is processed from the collimated light.

The invention disclosed could be practiced through the selection of respectively distinct band-pass filters of a number of frequency ranges. However, red and blue frequencies were selected in the preferred embodiment because this facilitates the use of commercially available cameras. Specifically, to separate the inspection container image, camera 18 is a color camera which acquires the composite image from both the diffuse illumination and the collimated illumination. Internal filters in color camera 18 separate the required image into three-color planes—red, blue and green. When interrogating the red plane, only the image from the collimated light is obtained. When interrogating the blue plane, only the image from the diffused light is obtained. This information is provided as a video signal from the color camera to the process computer for further processing and analysis at the process computer.

Also in accordance with the preferred embodiment, a band-pass filter 70 can be located between lens 20 and container 10. Filter 70 has been found to be useful in balancing the light intensity differences between diffused light and collimated light at lens 20. These light intensity differences are due to the nature of diffused light as well as differences in the pathways that the diffused light and the collimated light respectively travel. As an example, a filter 70 in the band-pass frequency range of light blue has sometimes been found helpful in better separating and processing the diffusion light image and the collimated light image.

As will be apparent to those skilled in the art, other embodiments of the invention disclosed herein may be included within the scope of the following claims.

We claim:

1. In a system for inspecting light-transmissive containers, apparatus for generating an image signal in response to a timing signal, said apparatus comprising:

a first light generator that emits light within a first predetermined frequency bandwidth in response to a timing signal;

a diffusion element that is illuminated by light emitted from said first light generator and that produces diffused light in response to light from said first light generator;

a second light generator that emits collimated light within a second predetermined frequency bandwidth in response to a timing signal; and a camera having a lens that is illuminated by diffused light from said diffusion element and that is also illuminated by collimated light from said second light generator, said camera having a first imaging means that generates an image signal in response to the diffused light within said first frequency bandwidth and having a second imaging means that generates an image signal in response to the collimated light within said second frequency bandwidth.

2. The apparatus of claim 1 further comprising:

a reflector that is illuminated by collimated light from said second light generator, said reflector being oriented with respect to said camera lens and with respect to said second light generator such that said reflector receives collimated light from said second light generator and redirects that light to illuminate the lens of said camera.

3. The apparatus of claim 1 wherein the first predetermined frequency bandwidth corresponds to the bandwidth of one of the colors red, blue and green in the visible spectrum.

4. The apparatus of claim 1 wherein the second predetermined frequency bandwidth corresponds to the bandwidth of one of the colors red, blue and green in the visible spectrum.

5. In a system for inspecting objects, apparatus for generating an image signal in response to a timing signal, said apparatus comprising:

a first light generator that is responsive to the timing signal, said first light generator emitting light within a first predetermined frequency bandwidth in response to the timing signal;

a second light generator that is also responsive to the timing signal, said second light generator emitting light within a second predetermined frequency bandwidth in response to the timing signal, wherein the frequencies of said second predetermined frequency bandwidth are outside the frequencies of said first predetermined frequency bandwidth;

a laminar element that has a diffusion laminate and a reflector laminate with said diffusion laminate contacting said reflector laminate to form an interface, said diffusion laminate being illuminated by light emitted by said first light generator to produce diffused light in response to light from said first light generator, said reflection laminate being illuminated by light emitted from said second light generator to produce collimated light in response to light from said second light generator; and a camera having a lens that is illuminated by diffused light from said diffusion laminate and that is also illuminated by collimated light from said reflector laminate, said camera having a first imaging means that generates an image signal in response to the diffused light within said first frequency bandwidth, said camera having a second imaging means that generates an image signal in response to the collimated light within said second frequency bandwidth.

6. The apparatus of claim 5 wherein said laminar element is oriented with respect to said camera lens such that said reflector laminate is located between said diffusion laminate and said camera lens.

7. The apparatus of claim 6 wherein said reflector laminate is partially transmissive to diffused light such that the diffused light produced by said diffusion laminate in response to light from said first light generator is transmitted through said reflector laminate from said diffusion laminate to said camera lens.

8. The apparatus of claim 7 wherein said reflector laminate comprises a transparent glass pane.

9. The apparatus of claim 8 wherein said glass pane has an outer surface and an inner surface that is oppositely disposed from said outer surface, the inner surface of said glass pane opposing the surface of said diffusion laminate.

10. The apparatus of claim 9 wherein the outer surface and the inner surface of said glass pane are substantially flat planar surfaces.

11. A system for inspecting objects that pass a predetermined inspection location, said system comprising:

a first light source;

a first filter that is illuminated by light from said first light source, said first filter rejecting light that is outside a first frequency bandwidth and passing light that is within said first frequency bandwidth;

a diffusion element that is located adjacent to said inspection location; said diffusion element being illuminated by light that is passed by said first filter and emitting diffused light in response to light from said first filter;

a second light source;

a second filter that is illuminated by light from said second light source; said second filter rejecting light that is outside a second frequency bandwidth and passing light that is within said second frequency bandwidth, where said second frequency bandwidth is separate from said first frequency bandwidth;

a collimated lens that is located adjacent to said inspection location, said collimated lens being illuminated by light that is passed by said second filter and emitting collimated light in response to light from said second filter; and a camera having a lens and having means for generating an electrical signal in response to light passing through said lens, said electrical signal generating means having first imaging means that is responsive to light that is within said first frequency bandwidth, said electrical signal generating means having a second imaging means that is responsive to light that is within said second frequency bandwidth, said camera lens being oriented to receive light from said diffusion element that passes through said inspection location and to receive light from said collimated lens that passes through said inspection location with said first imaging means being responsive to light from said diffusion element and passing through said camera lens and with said second imaging means being responsive to light from said collimated lens and passing through said camera lens.

12. A dual illumination source container inspection system comprising:

means for transporting containers through an inspection location;

a first light source that is located adjacent to said inspection location;

a first light filter that is illuminated by said first light source, said first light filter conducting light within a first frequency bandwidth;

a second light source that is also located adjacent to said inspection location;

a second light filter that is illuminated by said second light source, said second light filter conducting light within a second frequency bandwidth where said second frequency bandwidth is outside said first frequency bandwidth;

a lens that is illuminated by light that is conducted through said second light filter, said lens emitting substantially collimated light in response to said illumination by light that is conducted through said second light filter;

a laminar plate, said plate having a diffusion laminae and a reflection laminae, and that is located adjacent to said first light filter and adjacent to said second light filter, said laminar plate having a first external planer surface that is defined by said diffusion laminae and a second external planar surface that is defined by said reflection laminae, said laminar plate being oriented with respect to said first light filter such that the first major surface of said diffusing laminae being illuminated by light that is conducted by said first light filter and diffused by said diffusion laminae as it passes therethrough, said second external planar surface being illuminated by collimated light within said second bandwidth that is emitted from said lens, with said collimated light being reflected by the reflection laminae, said laminar plate being oriented such that the second planar surface is substantially 45° with respect to said collimated lens; and a camera that is located on the side of said conveyor that is opposite from the laminar plate, said camera having a lens that is illuminated by light that is emitted from said diffusion laminae and that is also illuminated by light that is emitted from said reflection laminae, said camera being responsive to light within said first bandwidth to produce a first image signal and also being responsive to light within said second bandwidth to produce a second image signal.

* * * * *